(12) United States Patent
Lee

(10) Patent No.: US 12,347,121 B2
(45) Date of Patent: Jul. 1, 2025

(54) ALIGNING METHOD BY GROUPED DATA

(71) Applicant: MEDIT CORP., Seoul (KR)

(72) Inventor: Dong Hoon Lee, Goyang-si (KR)

(73) Assignee: MEDIT CORP., Seoul (KR)

( * ) Notice: Subject to any disclaimer, the term of this patent is extended or adjusted under 35 U.S.C. 154(b) by 360 days.

(21) Appl. No.: 17/848,421

(22) Filed: Jun. 24, 2022

(65) Prior Publication Data
US 2022/0335628 A1    Oct. 20, 2022

Related U.S. Application Data

(63) Continuation-in-part of application No. PCT/KR2020/019090, filed on Dec. 24, 2020.

(30) Foreign Application Priority Data

Dec. 26, 2019 (KR) .................. 10-2019-0175292

(51) Int. Cl.
*G06T 7/30* (2017.01)
*A61B 5/00* (2006.01)
*G06T 15/08* (2011.01)

(52) U.S. Cl.
CPC ............... *G06T 7/30* (2017.01); *G06T 15/08* (2013.01); *A61B 5/0062* (2013.01);
(Continued)

(58) Field of Classification Search
CPC . G06T 7/30; G06T 15/08; G06T 2207/30036; G06T 2210/32;
(Continued)

(56) References Cited

U.S. PATENT DOCUMENTS 6,763,148 B1 * 7/2004 Sternberg ............... G06V 20/00
707/E17.02
8,209,144 B1 * 6/2012 Anguelov ............... G01C 15/00
702/95

(Continued)

FOREIGN PATENT DOCUMENTS

CN 102429740 A 5/2012
CN 104837436 A 8/2015
(Continued)

OTHER PUBLICATIONS

Non-final Office Action mailed on Mar. 28, 2024 from the Chinese Patent Office for Chinese Application No. 202080090581.6.
(Continued)

*Primary Examiner* — Negussie Worku
(74) *Attorney, Agent, or Firm* — Insight Law Group, PLLC; Seung Lee

(57) ABSTRACT

In an aligning method by grouped data according to the present disclosure, while initial grouped data is generated and a process of generating and aligning three-dimensional image data is performed, if a state in which pieces of three-dimensional volume data are not connected to each other continues for a predetermined time or longer, new grouped data is generated, so that at least one discontinuous grouped data may be generated. If three-dimensional volume data stored in new grouped data and three-dimensional volume data of previously generated grouped data are identified to have overlapping parts therebetween, an additional alignment step is performed to connect the overlapping parts to each other. As a result, a data gap is supplemented, and a patient's entire oral model data can be easily obtained.

13 Claims, 7 Drawing Sheets

(52) U.S. Cl.
CPC ... *A61B 5/0088* (2013.01); *G06T 2207/30036* (2013.01); *G06T 2210/32* (2013.01); *G06T 2210/41* (2013.01)

(58) Field of Classification Search
CPC ....... G06T 2210/41; G06T 2207/10016; G06T 2207/10021; G06T 2207/20221; G06T 7/579; A61B 5/0062; A61B 5/0088; A61C 9/0053; A61C 9/0046; A61C 13/0004; A61C 13/34; A61C 19/04
USPC .......................................................... 358/128
See application file for complete search history.

(56) References Cited

U.S. PATENT DOCUMENTS

| | | | | |
|---|---|---|---|---|
| 8,854,430 | B2 * | 10/2014 | Varslot | G01N 23/046 348/46 |
| 9,421,074 | B2 * | 8/2016 | Sachdeva | A61C 7/002 |
| 11,744,682 | B2 * | 9/2023 | Kopelman | G06T 7/0014 |
| 2013/0329020 | A1 | 12/2013 | Kriveshko et al. | |
| 2014/0016837 | A1 * | 1/2014 | Nechyba | G06V 40/45 382/118 |
| 2018/0005371 | A1 | 1/2018 | Sabina et al. | |
| 2018/0032786 | A1 * | 2/2018 | Tieu | G06V 40/13 |
| 2019/0046303 | A1 * | 2/2019 | Park | G16Z 99/00 |
| 2019/0147591 | A1 * | 5/2019 | Chang | G06F 30/20 382/128 |
| 2019/0192258 | A1 | 6/2019 | Kang et al. | |
| 2020/0105028 | A1 * | 4/2020 | Gao | G01J 3/508 |
| 2021/0401549 | A1 * | 12/2021 | Lee | A61B 5/45 |
| 2021/0401550 | A1 * | 12/2021 | Chang | A61C 13/00 |
| 2022/0330831 | A1 * | 10/2022 | Lee | G06T 15/08 |
| 2023/0076682 | A1 * | 3/2023 | Kim | A61B 6/5247 |

FOREIGN PATENT DOCUMENTS

| | | |
|---|---|---|
| CN | 109069097 A | 12/2018 |
| EP | 2258303 A1 | 12/2010 |
| KR | 10-2014-0109091 A | 9/2014 |
| KR | 10-1840444 B1 | 3/2018 |
| KR | 10-1930062 B1 | 3/2019 |
| KR | 10-1954487 B1 | 3/2019 |
| KR | 10-1953622 B1 | 5/2019 |
| KR | 10-2019-0118602 A | 10/2019 |
| KR | 10-2054901 B1 | 12/2019 |

OTHER PUBLICATIONS

International Search Report mailed Jun. 10, 2021 for International Application No. PCT/KR2020/019090 and its English translation.
Supplementary European Search Report dated Apr. 4, 2024 for European Application No. 20906611.7.
European Search Report dated Jul. 15, 2024 for European Application No. 20906611.7.

* cited by examiner

ALIGNING METHOD BY GROUPED DATA

CROSS-REFERENCE TO RELATED APPLICATIONS

This application is a Continuation-In-Part application of International Application No. PCT/KR2020/019090, filed Dec. 24, 2020, which claims the benefit of Korean Patent Application No. 10-2019-0175292, filed Dec. 26, 2019 in the Korean Intellectual Property Office, the disclosures of which are incorporated herein in their entirety by reference.

TECHNICAL FIELD

The present disclosure relates to an aligning method by grouped data, and more specifically, to an aligning method by grouped data, which continuously performs a scan by generating a new group when three-dimensional volume data are not connected to each other in an aligning process while scanning an inside of an oral cavity.

BACKGROUND ART

Conventionally, the impression of a patient's oral cavity is acquired using an alginate, and plaster or the like is poured into an acquired mold to produce the patient's tooth model. However, when the patient's tooth model is produced, the accuracy of the model may be problematic, and there is a disadvantage in that when a precise model may not be produced, it is difficult to customize treatment for the patient in making a prosthetic treatment product to be applied to the patient.

Recently, the inside of the patient's oral cavity is scanned using a three-dimensional scanner, and the scanned part is acquired as three-dimensional data, so that accurate dimensions and a shape of the inside of the oral cavity may be obtained, and the user may accurately diagnose the patient, and an appropriate prosthetic treatment may be provided to the patient.

A user (a therapist, usually, a dentist) grips an intraoral scanner among three-dimensional scanners and draws a part of the scanner into or out from the oral cavity to capture the patient's affected parts (which may include teeth, gums, etc. inside the oral cavity). The intraoral scanner acquires the patient's captured affected part as image data, converts the image data into three-dimensional volume data using the brightness information of each data, and aligns the overlapping parts to finally generate one three-dimensional model. At this time, one three-dimensional model may mean the entire intraoral model data of the patient acquired by capturing the maxilla, mandible, and occlusal state of the patient. However, when the aligning process is performed, there may occur a case in which the alignment is interrupted when the user does not carefully scan. There is a problem in that when the alignment is interrupted, the coupling between the three-dimensional volume data becomes incomplete, so that the precision of the patient's entire intraoral model data is lowered.

SUMMARY OF INVENTION

Technical Problem

An object of the present disclosure is to provide an aligning method by grouped data, which classifies data into at least one grouped data and supplements a data gap occurring between the grouped data in an additional alignment operation by newly generating and separating a group in which data is stored when the alignment is not performed for a certain time or more in converting images acquired from an imaging unit into three-dimensional volume data and performing the alignment.

Solution to Problem

An aligning method by grouped data according to the present disclosure may include generating a first grouped data including at least one first image data through a scanner, determining whether a second image data is aligned with the first grouped data by a control unit, including the second image data in the first grouped data when the second image data is aligned with the first grouped data by a control unit, generating a second grouped data to include the second image data when the second image data is not aligned with the first grouped data by a control unit, and combining the first grouped data and the second grouped data by a control unit.

In addition, the first image data and the second image data may be converted into three-dimensional volume data.

In addition, the attempting of the alignment may include confirming whether the second image data is aligned with the first grouped data for the predetermined time, and updating the number of alignment attempts when the second image data is not aligned with the first grouped data in the confirming of whether the second image data is aligned with the first grouped data.

In addition, the process may further include confirming whether the updated number of alignment attempts is less than the critical number of times by the control unit, and return to confirming whether the second image data is aligned with the first grouped data when the number of alignment attempts is less than the critical number of times.

In addition, the control unit may generate the second grouped data to include the second image data when the number of alignment attempts is greater than or equal to the critical number of times.

In addition, in the combining of the first grouped data and the second grouped data, at least a partial area of the first image data included in the first grouped data and at least a partial area of the second image data included in the second grouped data may be aligned.

In addition, the first image data and the second image data may be aligned through a third image data that overlaps each of the at least the partial area of the first image data and the at least the partial area of the second image data.

Meanwhile, an aligning method by grouped data according to another embodiment of the present disclosure may include an image generating operation of acquiring an image along a scan path through a scanner, an aligning operation of aligning the image data continuously acquired along the scan path to be connected to each other by a control unit, a grouped data storing operation of making the image data a grouped data and categorizing and storing the grouped data based on a point at which the image data are disconnected to each other in the aligning operation by the control unit, and a reconnection determining operation of aligning data of the two or more grouped data to be connected to each other by the control unit.

In addition, the point at which the image data are disconnected may be determined according to an overlapping range of the continuous image data in the grouped data storing operation.

In addition, the scan path may include a plurality of paths, the plurality of paths may have different start points and end points, and the plurality of paths may have a scan area overlapping in at least some sections.

In addition, the number of grouped data stored in the grouped data storing operation may have the number according to the plurality of scan paths.

In addition, the point at which the image data are disconnected to each other in the aligning operation may be the end point of each scan path.

In addition, the method may further include displaying the point at which the image data is disconnected to each other between the grouped data on a display unit by the control unit.

Advantageous Effects of Invention

By using the aligning method by grouped data according to the present disclosure, all data do not need to be continuously aligned and thereafter, the additional alignment process is performed, and as a result, it is possible to derive the entire intraoral model data and reduce the burden that the user should necessarily continuously scan the inside of the oral cavity.

In addition, it is possible to supplement and minimize the data gap by comparing and overlapping the image data stored in the new grouped data with the image data of the previously generated grouped data, thereby improving the reliability of the data acquired through the scanner.

In addition, it is possible to minimize the range to be additionally scanned by the user by scanning only between the grouped data in which the data gap has occurred.

DESCRIPTION OF EMBODIMENTS

Figure 1:
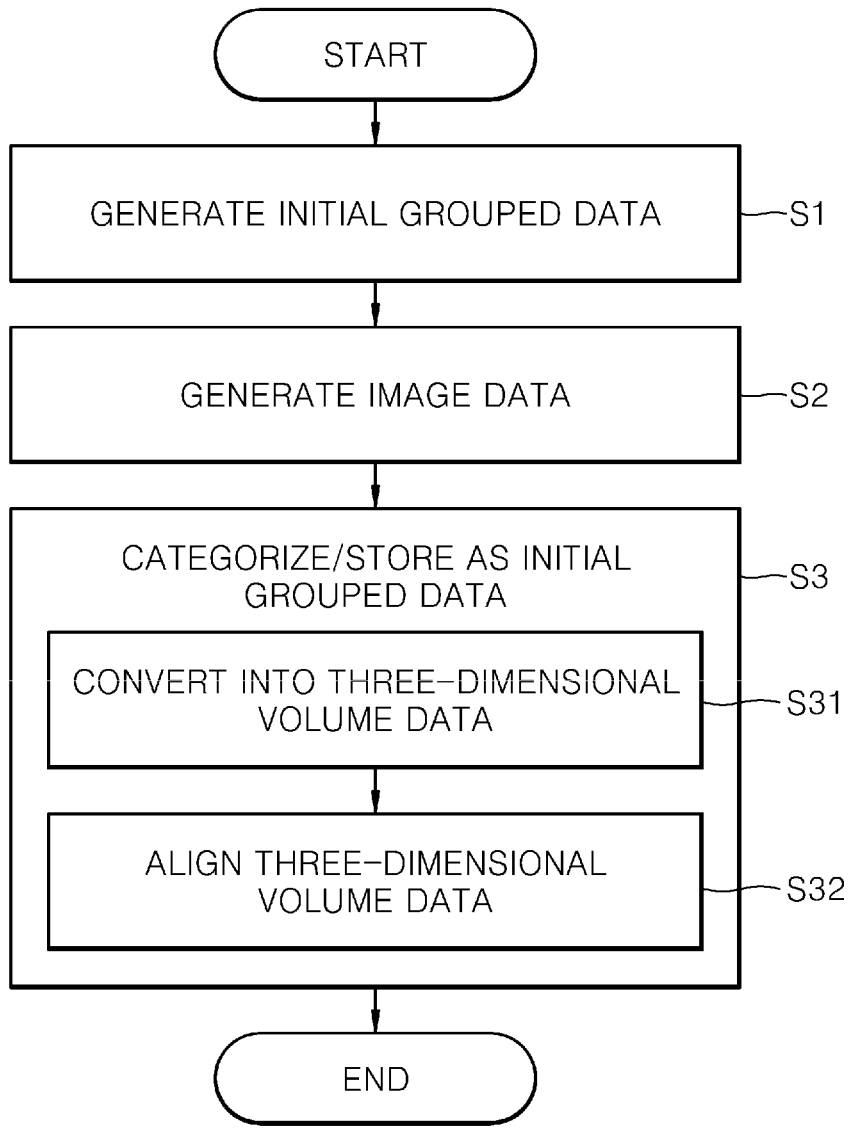
FIG. 1 is a flowchart of an aligning method by grouped data according to the present disclosure.

Advantages and features of the present disclosure, and methods for achieving them, will become apparent with reference to the embodiments described below in detail in conjunction with the accompanying drawings. However, the present disclosure is not limited to embodiments disclosed below but will be implemented in various different forms, and only these embodiments are provided so that the disclosure of the present disclosure will be thorough and complete and will fully convey the scope of the present disclosure to those skilled in the art to which the present disclosure pertains, and the present disclosure is defined by the description of the claims. Throughout the specification, the same configurations are denoted by the same reference numerals.

Hereinafter, an embodiment of the present disclosure will be described in detail with reference to the drawings.

Figure 2:
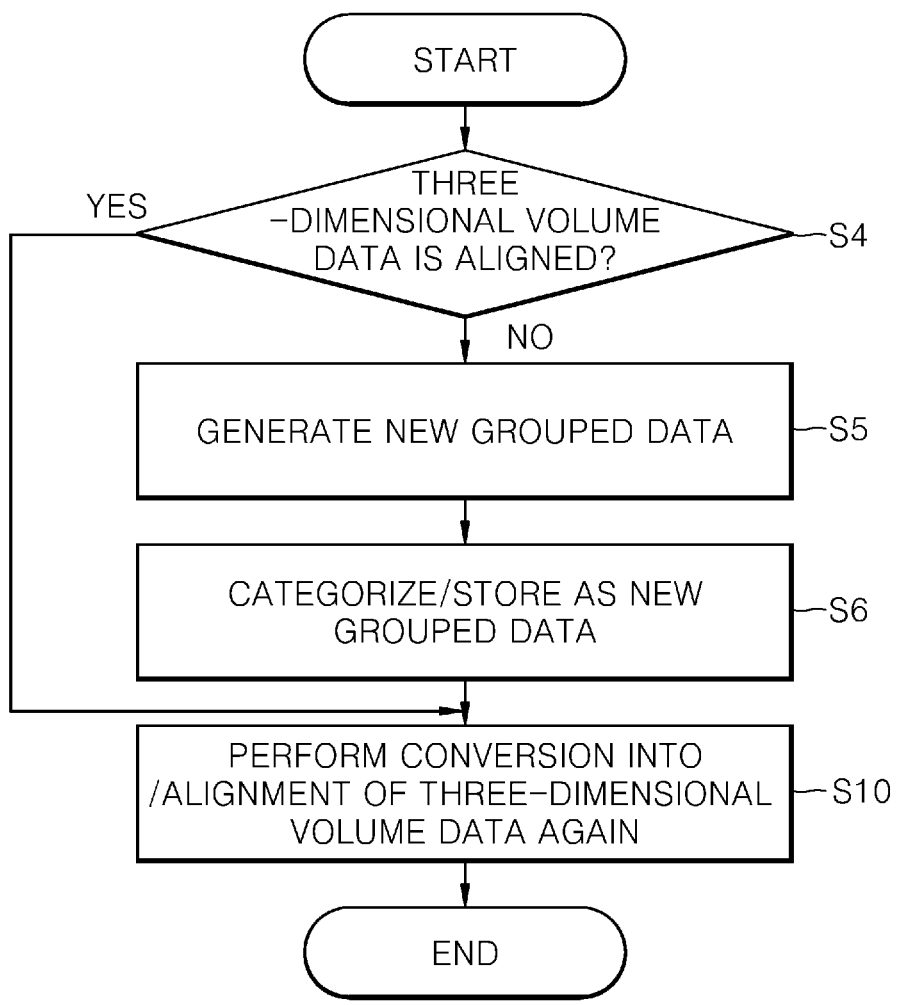
FIG. 2 is a flowchart of the aligning method by grouped data according to the present disclosure.
Figure 3:
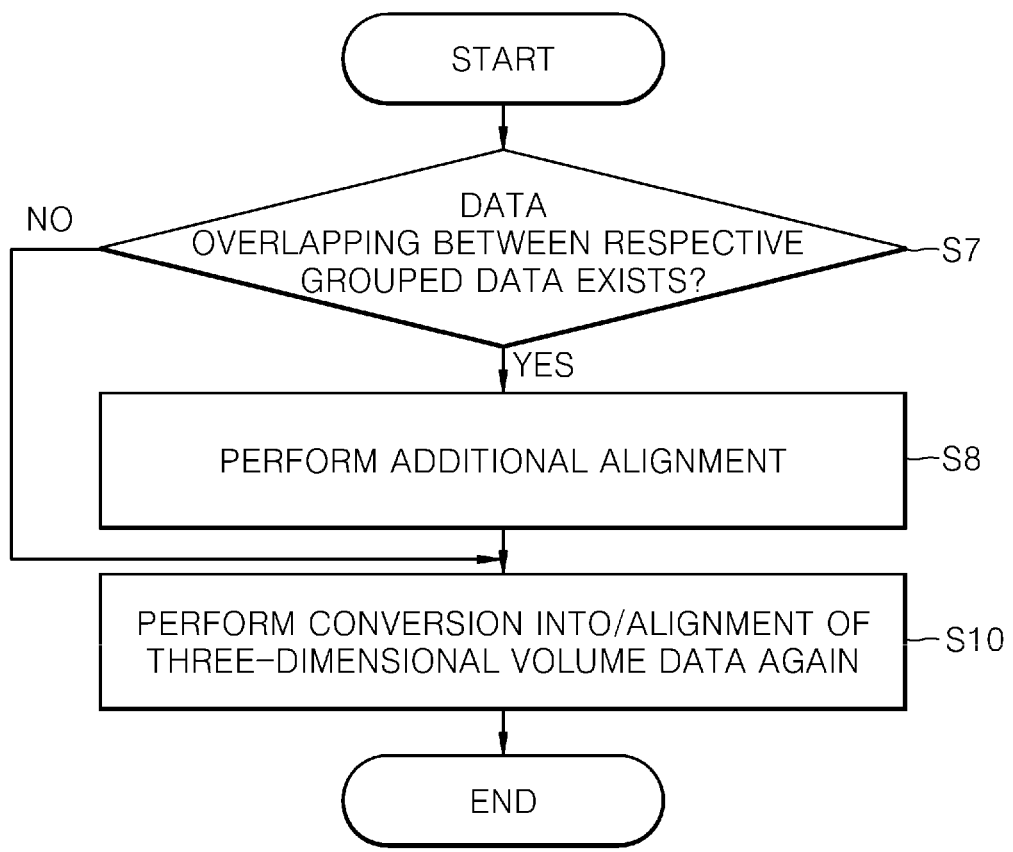
FIG. 3 is a flowchart of the aligning method by grouped data according to the present disclosure.

FIGS. 1 to 3 are flowcharts of an aligning method by grouped data according to the present disclosure.

Referring to FIG. 1, the aligning method by grouped data according to the present disclosure includes an initial grouped data generating operation (S1) in which an initial grouped data is generated. When a user (usually a person who treats a patient or who may be a dentist) starts to scan an affected part of the patient (in the present disclosure, which usually means an inside of an oral cavity of the patient, and which may be teeth, gums, or the like to be captured for treatment such as implants, crowns, orthodontics) through a scanner, the initial grouped data is generated. A point at which the initial grouped data is generated may also be performed by a processor built in the scanner or performed by a processor built in a control unit (e.g., a personal computer) connected to the scanner. It is preferable that the initial grouped data is generated in the processor formed inside the scanner. Meanwhile, since the initial grouped data means a first grouped data, it may be used interchangeably with the first grouped data for convenience in the following description.

In addition, when the user scans the inside of the patient's oral cavity through the scanner, light reflected from the teeth or gums inside the oral cavity is incident into the scanner through an opening formed at one end of the scanner. Light incident into the scanner is accommodated by at least one imaging unit formed inside the scanner. At this time, the imaging unit may include a single camera composed of one camera or a multi-camera including two or more cameras. When the imaging unit includes two or more multi-cameras, two or more images may be acquired at one time point, so that it is possible to acquire more precise image data.

Light incident on the camera may be generated as an image data by an imaging sensor electrically connected to the camera (S2). In other words, the imaging unit may include a camera and an imaging sensor electrically connected to the camera, and image data may be generated by the imaging unit. At this time, the image data may have the form of a two-dimensional image or may also be a voxel data that is a three-dimensional volume data. The image data generated by the imaging sensor may be categorized and stored as the initial grouped data (S3). In other words, when the image data is generated through the capturing, the generated image data is categorized and stored as the initial grouped data (or first grouped data). A path where the image data is stored may also be a storage device of a personal computer spaced apart from the scanner or may also be a storage unit built into the scanner itself.

Meanwhile, the initial grouped data storing operation (S3) may include a three-dimensional data converting operation (S31) of converting the image data acquired in the image generating operation (S2) into a three-dimensional volume data. The three-dimensional data converting operation (S31) may convert the two-dimensional image data acquired from the imaging unit into 3-dimensional data including a voxel data including brightness information in a pixel having a volume using brightness information of a corresponding part. In addition, the three-dimensional volume data formed from the three-dimensional data converting operation (S31) may be aligned so that overlapping parts are connected to form a larger chunk of data (S32). At this time, the alignment may mean that two or more three-dimensional volume data are merged into one three-dimensional volume data having a larger volume by the connection between three-dimensional volume data at minimum. In the aligning process, a set of three-dimensional volume data for one entire mandible, a set of three-dimensional volume data for one entire maxilla, and a set of three-dimensional volume data for occlusion may be formed, and these data sets are combined to generate one complete data set for the patient's intraoral model. At this time, the three-dimensional data may be converted by an external processor (i.e., control unit) that is formed outside the scanner, electrically connected to the scanner, and receives the image data captured and generated by the scanner.

When the above-described aligning operation (S32) is performed, a continuous aligning process may not be performed due to the user's inexperienced scan or for the user's intentional distinction. Conventionally, when the aligning process is not performed, the aligned result according to the user's scan may be displayed on a screen having a red edge of a display unit. When the aligned result is displayed as described above, an additional data is not acquired unless the three-dimensional volume data is generated by scanning a part overlapping the previous scan area that may be aligned.

In order to solve the above problem, the aligning method by grouped data according to the present disclosure may further include a disconnect determining operation (S4) of determining whether a state in which the alignment is not performed continues for a certain time or more while the three-dimensional volume data are connected to each other in the aligning operation. At this time, when the state in which the alignment is not performed continues for the certain time or more, it means maintaining a state in which the three-dimensional volume data is previously generated and the alignment is performed by the overlapping data parts and then the overlapping data parts do not appear, so that the data are not overlapped and the alignment is not performed. The certain time may mean a specific time previously set in a program, but preferably, may be set to a time with an interval at which it is determined that the aligning process is not reasonably performed while the user performs the scan.

Meanwhile, the expression "disconnect" used herein should be construed as not meaning a state in which the scanner equipment is electrically disconnected to a personal computer, a server, or a power source, but meaning a state in which data are disconnected because there is no overlapping parts between the three-dimensional volume data. Meanwhile, since the three-dimensional volume data are connected by an external processor (i.e., control unit), whether to determine the disconnect may also be performed by the external processor.

In the disconnect determining operation (S4), when it is determined that the disconnect state continues for the certain time or more because there is no overlapping parts between the three-dimensional volume data, the data collection of the initial grouped data (first grouped data) is terminated, and a three-dimensional volume data lastly connected may be set to a last data.

Figure 4:
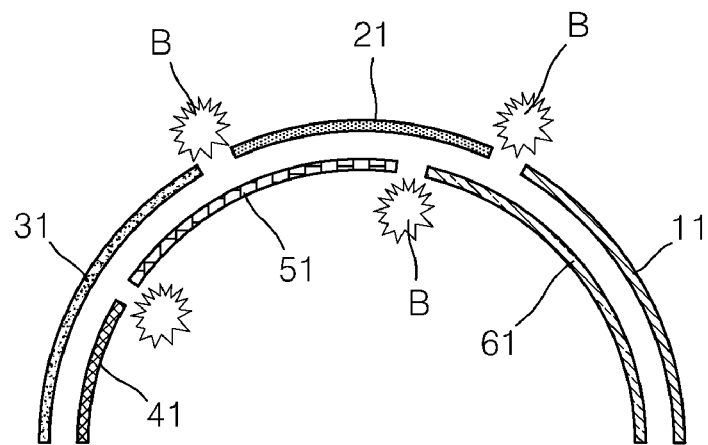
FIG. 4 is a view conceptually showing the aligning method by grouped data according to an embodiment of the present disclosure.
Figure 5:
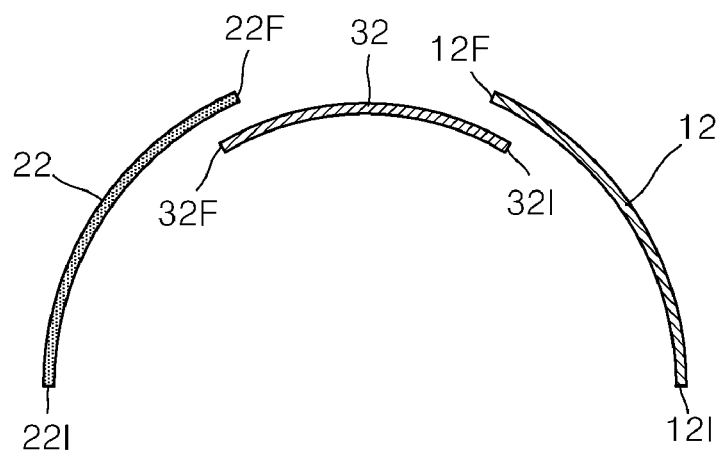
FIG. 5 is a view conceptually showing the aligning method by grouped data according to an embodiment of the present disclosure.
Figure 6:
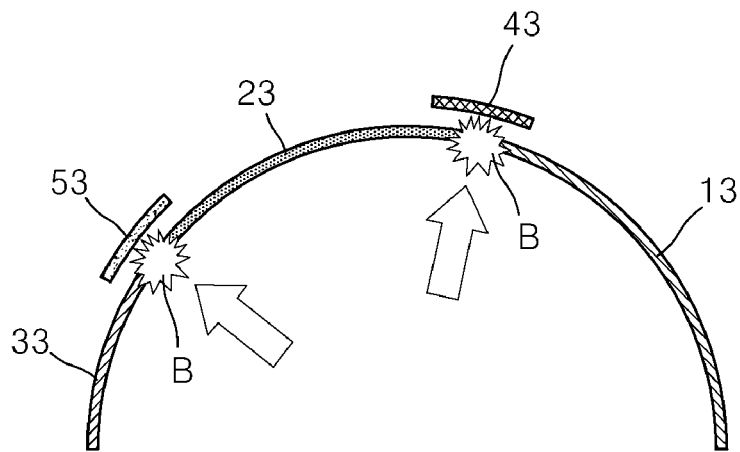
FIG. 6 is a view conceptually showing the aligning method by grouped data according to an embodiment of the present disclosure.

FIGS. 4 to 6 are views conceptually showing an embodiment of the aligning method by grouped data according to the present disclosure.

As described above, when the previous data collection of the grouped data is terminated because the three-dimensional volume data is disconnected due to having no overlapping parts therebetween in the disconnect determining operation, a new grouped data may be generated by the control unit (S5). At this time, the new grouped data generated just after the initial grouped data may be named a second grouped data. The second grouped data may form a data set formed to be spaced apart from the first grouped data.

When the new grouped data is generated, the image data generated by the imaging unit of the scanner is now categorized and stored as the new grouped data by the control unit (S6). In other words, the image data generated after the second grouped data has been generated may be categorized and stored as the second grouped data. As described above, when the image data is serially categorized and stored as the second grouped data and then it is determined that the state in which the three-dimensional volume data are disconnected continues for the certain time or more because there is no overlapping parts therebetween (the disconnect determining operation), the storage of the image data as the second grouped data is terminated to generate a third grouped data, and an image data generated thereafter is categorized and stored as the third grouped data by the control unit. These grouped data may also be stored in the storage device of the personal computer spaced apart from the scanner or stored in the storage unit built into the scanner itself.

Meanwhile, as described above, as the initial grouped data (first grouped data) and the new grouped data (second grouped data, third grouped data, and the like) are continuously generated, the data are discontinuously collected even when the aligning process is not continuously performed. At this time, the "the data is discontinuously collected" means that the data are not overlapped between the respective grouped data, and there is the continuity between the three-dimensional volume data within each grouped data because the aligning operation has been performed therebetween. However, since the user is required to finally acquire the patient's entire intraoral model data, it is necessary to supplement a data gap B between the respective grouped data through subsequent additional scans.

Accordingly, the aligning method by grouped data according to the present disclosure may further include a reconnection determining operation (S7) of checking whether the data of the initial grouped data and the new grouped data overlap by the control unit. Referring to FIG. 4, the user performs measurement from right to left based on FIG. 4. At this time, an image data of a first grouped data 11 is initially converted into a volume data and an alignment is performed, and then a new second grouped data 21 is generated through the disconnect determining operation, and a second grouped data storing operation is performed, and an image data generated after the second grouped data storing operation is started is categorized and stored as the second grouped data 21. A part where the data is not generated because the capturing is not performed between the first grouped data 11 and the second grouped data 21 is left as the data gap B.

In the same manner, the data gap B is left between the second grouped data 21 and a third grouped data 31. The user performs the scan again from left to right to supplement the data gap B. For example, by supplementing the data gaps B present between the respective grouped data 11, 21, 31, 41, 51, and 61 as a fourth grouped data 41, a fifth grouped data 51, and a sixth grouped data 61 are generated, it is possible to eventually acquire the entire intraoral model data of the patient.

Referring to FIG. 5, when the first grouped data 12 is generated and the scan is started by the scanner, a data initially generated in the first grouped data 12 is referred to as a first group initial data 121. Meanwhile, in the disconnect determining operation, when the state in which the three-dimensional volume data are disconnected to each other continues for the certain time or more and the second grouped data 22 is generated, the three-dimensional volume data generated and stored in the first grouped data 12 lastly before the second grouped data 22 is generated becomes a first group final data 12F. For the same purpose, a data initially generated in the second grouped data 22 becomes a second grouped initial data 221, and a three-dimensional volume data generated and stored in the second grouped data 22 lastly when the third grouped data 32 is generated becomes a second grouped final data 22F.

Meanwhile, when the third grouped data 32 is generated and the new data storing operation is performed, a third grouped initial data 321 overlaps the first grouped data 12 previously captured and generated as the three-dimensional volume data by the control unit. Accordingly, the three-dimensional volume data stored in the third grouped data 32 may be connected to the three-dimensional volume data stored in the first grouped data 12 (the additional alignment operation by an alignment unit of the control unit (S8)), and supplement the data gap B between the first grouped data 12 and the second grouped data 22 previously present.

In order to supplement the data gap B as described above, the alignment unit of the control unit may determine whether three-dimensional volume data stored in the new grouped data overlaps any one of the three-dimensional volume data of the previously generated grouped data (S7). Preferably, it may be determined whether the initial data or final data of the new grouped data overlaps the three-dimensional volume data of the previously generated grouped data by the alignment unit of the control unit. As exemplarily shown in FIG. 5, the initial data 321 of the third grouped data 32 overlaps the three-dimensional volume data of the first grouped data 12, a final data 32F of the third grouped data 32 is overlapped and additionally aligned with the three-dimensional volume data of the second grouped data 22 to eventually supplement the data gap B part (S8). As described above, by comparing and overlapping the data stored in the new grouped data with the three-dimensional volume data of the previously generated grouped data, it is possible to supplement and minimize the data gap B, thereby improving the reliability of the data acquired through the scanner. Meanwhile, even while the new grouped data storing operation (S6) or the additional alignment operation (S8) is being performed, the control unit may again perform an operation of continuously converting the image data acquired by the scanner into the three-dimensional volume data and aligning the three-dimensional volume data (S10). Meanwhile, the reconnecting determination operation, the additional alignment operation, and the like may be performed together on the external processor (i.e., control unit) configured to determine disconnect and perform alignment.

Referring to FIG. 6, the first grouped data 13, the second grouped data 23, and the third grouped data 33 have been generated and the scan has been performed, but the data gaps B has occurred between the classified respective grouped data 13, 23, and 33. Accordingly, the user is required to scan a wide area again after the conventional alignment error occurrence part, but by additionally scanning only between the first grouped data and the second grouped data (between reference numerals 13 and 23) and between the second grouped data and the third grouped data (between reference numerals 23 and 33) in which the data gaps B occur using the scanner through the aligning method by grouped data according to the present disclosure, it is possible to minimize a range to be scanned.

Figure 7:
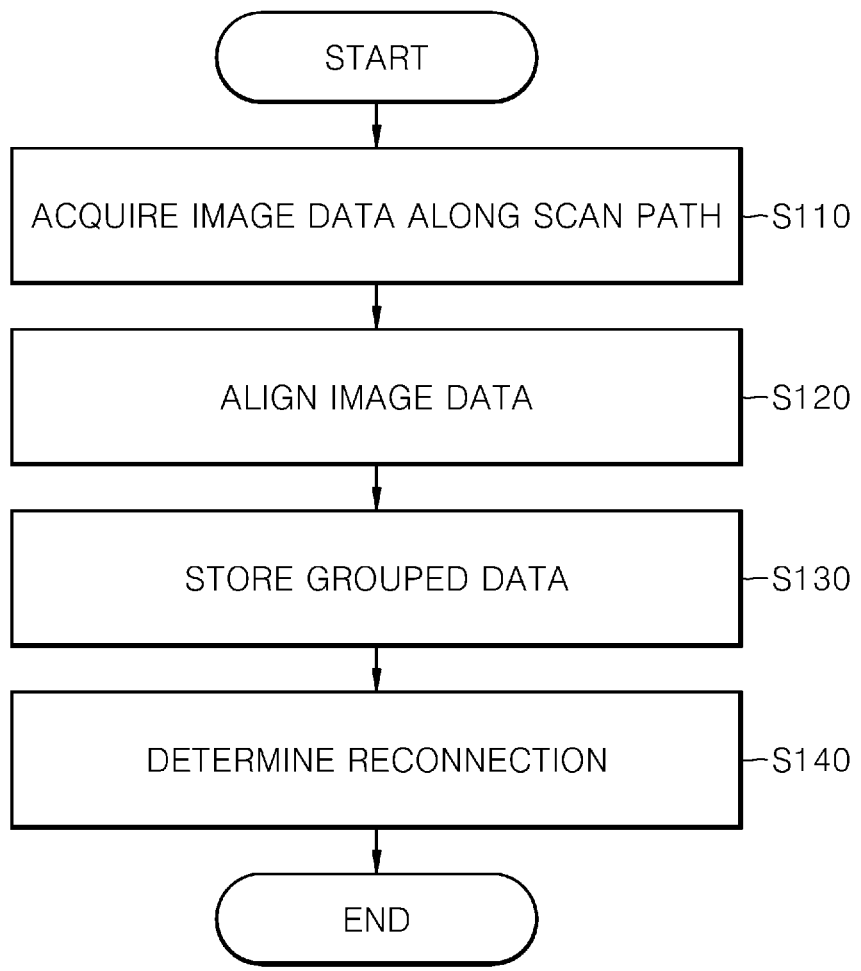
FIG. 7 is a flowchart of an aligning method by grouped data according to another embodiment of the present disclosure.

FIG. 7 is a flowchart of an aligning method by grouped data according to another embodiment of the present disclosure. Referring to FIG. 7, an aligning method by grouped data according to another embodiment of the present disclosure may include an image generating operation (S110) of acquiring an image data along a scan path through a scanner, and an aligning operation (S120) of aligning the image data continuously acquired along the scan path to be connected to each other by a control unit. As described above, when the inside of the patient's oral cavity is scanned through the intraoral scanner, the image data for an object to be scanned (which means the parts inside the oral cavity) is generated. The image data may be an image data in which light reflected from the object to be scanned is incident into the intraoral scanner and digitalized through the imaging unit formed inside the intraoral scanner. In addition, when the image data is continuously acquired along the scan path, overlapping areas occur between the continuous image data, and these overlapping areas may be connected and aligned with each other to appear as one connected image data again by an alignment unit of the control unit. As a result, when the aligning operation is normally performed, one mandibular data, one maxillary data, and occlusal data obtained by combining the mandibular and maxillary data may be integrated as a whole to generate the entire intraoral model data of the patient. Meanwhile, the generated image data may be stored in the storage unit that may be formed inside the scanner or a storage device that is one component of the control unit.

Meanwhile, an aligning method by grouped data according to another embodiment of the present disclosure may further include a grouped data storing operation (S130) of classifying the image data into different grouped data based on the point at which the image data are disconnected to each other and categorizing and storing the grouped data in the aligning operation by the alignment unit. While the above-described aligning operation is performed, there is a case in which the connection and alignment between the image data may not be performed because the scanning is not sufficiently performed to form the overlapping parts between the image data. In other words, in the aligning method by grouped data according to another embodiment of the present disclosure, a case in which the data gap B occurs because the overlapping range of the image data is not sufficiently formed regardless of whether the connection state of the image data continues for the certain time may be defined as the disconnect. Meanwhile, the grouped data generated by a grouped data management unit of the control unit may be stored in the storage unit that may be formed inside the scanner or the storage device that is one component of the control unit.

When the disconnect state occurs by the determination of the alignment unit of the control unit as described above, the (intraoral) scanner may categorize the image data connected before the disconnect state as an nth grouped data to store the categorized grouped data in the storage unit built in in the scanner or the storage device of the control unit, and the grouped data management unit of the control unit categorizes the image data after the disconnect state as an (n+1)th grouped data to store the categorized grouped data in the storage unit built in in the scanner or the storage device of the control unit. At this time, n may be any natural number, which means that it may have a plurality of grouped data until the scan is performed from the first grouped data to the final grouped data.

For example, as shown in FIG. 4, there is one scan path connecting the first grouped data 11, the second grouped data 21, and the third grouped data 31, and when the disconnect occurs twice, that is, when the data gap B occurs during the scan, three grouped data (reference numerals 11, 21, and 31) are generated. Likewise, while one scan path connecting the fourth grouped data 41, the fifth grouped data 51, and the sixth grouped data 61 is scanned, when the disconnect (a state in which the data gap has occurred) occurs twice, three grouped data (reference numerals 41, 51, and 61) are generated. As a result, describing with an example of FIG. 4, while the scan path is scanned twice in total, the disconnect occurs twice for each scan path, so that a total of six grouped data may be generated.

Meanwhile, in the grouped data storing operation, the grouped data is classified before and after the time point when a current state is determined as the disconnect state, and the image data acquired just before the current state is determined as the disconnect state becomes the final data of the corresponding grouped data, and the image data acquired just after the current state is determined as the disconnect state becomes the initial data of the corresponding grouped data by an operation of the grouped data management unit of the control unit. When this is interpreted in terms of the scan path, the point scanned just before the current state is determined as the disconnect state is recognized as the end point of the corresponding scan path, and the point scanned just after the current state is determined as the disconnect state is recognized as the start point of the corresponding scan path. In addition, as described above, when the current state is determined as the disconnect state and the image data are classified into different grouped data, it means that the two classifications have different start points and end points. This means that the disconnected points become the end points of the respective scan paths.

As shown in FIG. 5, the categorization of the image data into the plurality of grouped data by the grouped data management unit of the control unit is to distinguish the scan paths between the respective grouped data, so that the number of grouped data stored in the grouped data storing operation may correspond to the number of scan paths. For example, the disconnect occurs at the end point 12F of the scan path corresponding to the first grouped data 12 to generate the first grouped data 12, the disconnect occurs at the end point 22F of the scan path corresponding to the second grouped data 22 to generate the second grouped data 22, and lastly, the disconnect occurs at the end point 32F of the scan path corresponding to the third grouped data 32 to generate the third grouped data 32. As described above, when the scan is performed with three scan paths when the inside of the patient's oral cavity is scanned, a total of three grouped data may be generated.

The user continuously performs the scan through the scanner to acquire the complete intraoral model data of the patient by minimizing the data gap B. When the scan is continuously performed, the image data corresponding to subsequent grouped data may have a part overlapping the image data corresponding to the previous grouped data. In other words, this means that the plurality of scan paths may have the scan areas overlapping each other in at least some sections, and at this time, the data gap B may be filled.

Referring to FIG. 5, when the grouped data corresponding to the number of scan paths are generated, this is generally a case in which the scan path is intentionally classified according to the user's convenience (i.e., a first scan may be performed through the scan path corresponding to the first grouped data 12 and then a second scan may be performed through the scan path corresponding to the second grouped data 22, and lastly, a third scan may be performed through the scan path corresponding to the third grouped data 32), so that this case may generally have the scan areas overlapping each other between at least two or more scan paths, so that the data gap B may be filled.

As described above, when the data gap B is filled, it means that the image data may be connected between different grouped data, and a reconnection determining operation (S140) of confirming the possibility of connecting and aligning the data of two or more grouped data again and aligning the data to be connected to each other may be included. The reconnection determining operation (S140) may be performed by the alignment unit of the control unit. In the reconnection determining operation, by aligning the three-dimensional data included in different grouped data with respect to the data for the part where the data gap B has occurred, the entire data may be supplemented, and by continuously performing the scan as described above, it is possible to minimize the data gap B and as a result, complete the complete intraoral model data of the patient.

Meanwhile, the above-described alignment, disconnect determination, reconnection determination, and data supplementation between the image data or the three-dimensional volume data may be performed by the control unit (e.g., the external processor) formed outside the scanner.

Meanwhile, the aligning method by grouped data according to another embodiment of the present disclosure may further include displaying on a display unit the point at which the data gap B where the image data are disconnected to each other between the grouped data has occurred. Referring to FIG. 6, a data gap indication unit that is one component of the control unit may display the point at which the data gap B has occurred in a predetermined shape (e.g., an arrow shape). In the aligning method by grouped data according to another embodiment of the present disclosure, the data gap indication unit may display the point of the data gap B on the display unit with the arrow or the like so that the user may clearly confirm the point of the data gap B, the user may scan only the part where the data gap B has occurred again through the scanner to minimize the data gap B, and the alignment unit of the control unit may connect the data between the grouped data to each other. The display unit may mean a display device electrically connected to the scanner or the external processor, and may be a display device having a screen for notifying a user of whether the data gap B has occurred.

Hereinafter, an aligning method by grouped data according to still another embodiment of the present disclosure will be described.

Figure 8:
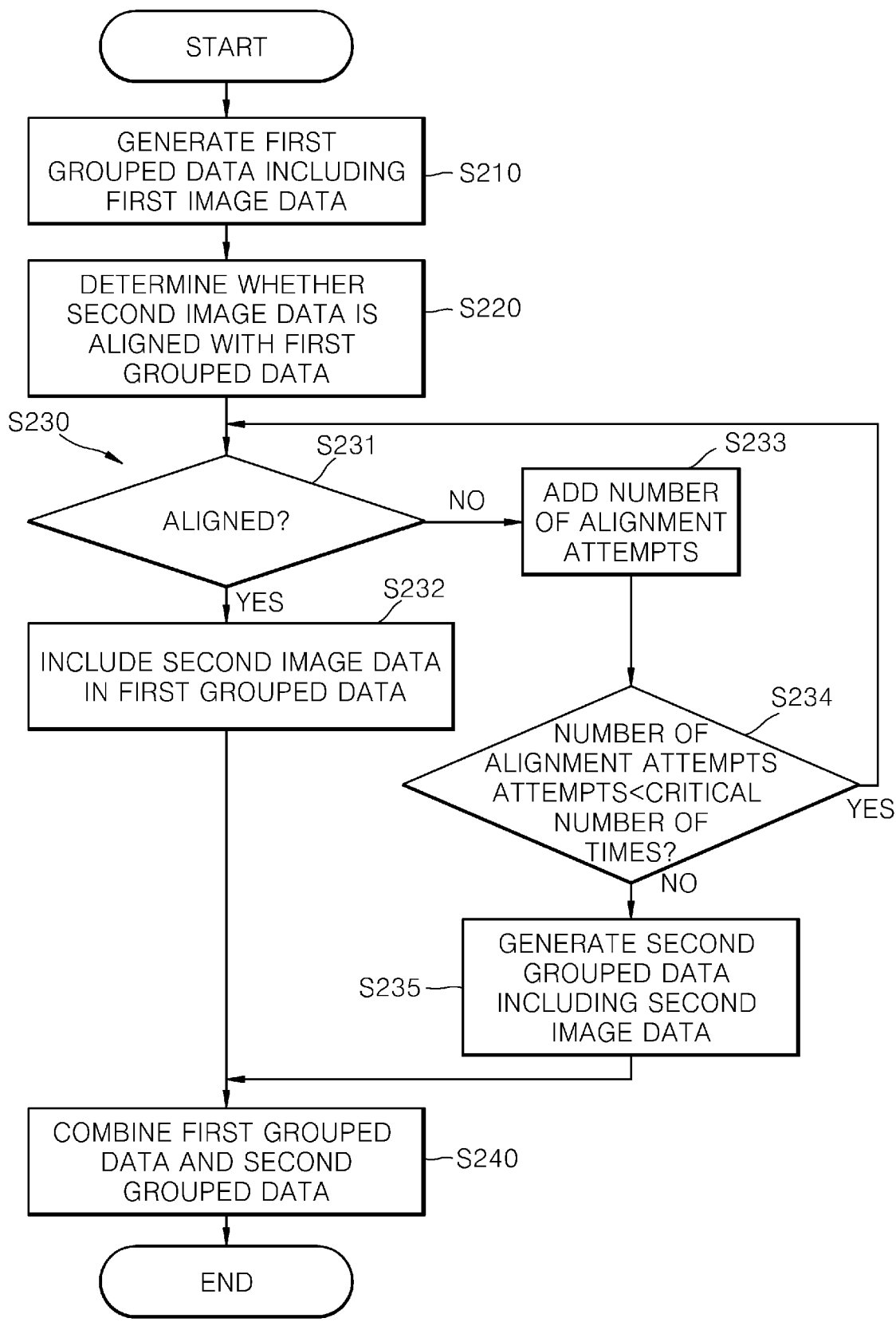
FIG. 8 is a flowchart of an aligning method by grouped data according to still another embodiment of the present disclosure.

FIG. 8 is a flowchart of an aligning method by grouped data according to still another embodiment of the present disclosure.

Referring to FIG. 8, the aligning method by grouped data according to still another embodiment of the present disclosure includes an operation of generating the first grouped data including at least one first image data through a scanner (S210) and an operation of determining whether a second image data is aligned with the first grouped data through a control unit (S220). When the scan process is started, at least one image data may be acquired by the scanner, and the image data may form one or more grouped data. For example, a category of the first grouped data is generated, and the image data is included in the first grouped data as the first image data. At this time, the image data (the first image data and the second image data) may be two-dimensional or three-dimensional data.

In the operation of generating the first grouped data (S210), at least one first image data may be aligned to form one three-dimensional volume data by the control unit. More specifically, in the operation of generating the first grouped data (S210), a three-dimension conversion unit of the control unit may convert two-dimensional data into three-dimensional data, and the alignment unit of the control unit may mutually align the converted three-dimensional data to form the aligned three-dimensional volume data. When two or more image data are sequentially acquired, the lastly acquired image data may be aligned along with the three-dimensional volume data formed by aligning the previously acquired image data. According to this process, the three-dimensional volume data may be expanded. In other words, one grouped data may be generated as one three-dimensional volume data by aligning at least one image data. In other words, the sequentially acquired image data may be aligned by the alignment unit of the control unit and generated as one three-dimensional volume data.

Meanwhile, in the operation of determining whether the second image data is aligned with the first grouped data (S220), the alignment unit of the control unit may determine whether the first image data is included in the first grouped data, and the second image data acquired in the scan process using the scanner is aligned with at least any one of the first image data. For example, it may be determined whether the second image data may overlap at least some of the first image data to be connected and aligned by the alignment unit.

For the determination, the second image data may attempt to be aligned with at least some areas of the first image data included in the first grouped data the predetermined number of times or for a predetermined time by the alignment unit of the control unit (S230). For example, the operation of attempting the alignment (S230) includes confirming whether the second image data is aligned with the first grouped data for the predetermined time (S231). When the second image data is aligned with the first grouped data within a preset time, the second image data may be included in the first grouped data (S232). In other words, the second image data may be aligned with at least some of the first image data included in the first grouped data to expand the three-dimensional volume data of the first grouped data. When the second image data is aligned with the first grouped data, the grouped data management unit of the control unit may include the second image data in the first grouped data.

Meanwhile, when the scan is performed, the data gap may occur because the scan areas do not overlap. The data gap may occur when the user has not carefully scanned the patient's oral cavity or has not intentionally performed the scan continuously. In this case, the grouped data management unit of the control unit may include the image data acquired before the data gap occurs in any one grouped data, and include the image data acquired after the data gap has occurred in the new grouped data.

A process of classifying the grouped data will be described in more detail. When the second image data is not aligned with the first grouped data for the predetermined time, the alignment unit may update the number of alignment attempts (S233). For example, the number of initial alignment attempts may be set to 1. At this time, when the second image data is not aligned with the first grouped data for the predetermined time in the operation of confirming whether the second image data is aligned with the first grouped data (S231), the alignment unit may add the number of alignment attempts by one.

After the number of alignment attempts is updated, an operation of confirming whether the updated number of alignment attempts is less than the critical number of times (S234) may be performed. For example, the critical number of times may be 10, and when the updated number of alignment attempts is less than 10, the control unit may return to the operation of confirming whether the second image data is aligned with the first grouped data (S231) again, and the alignment unit of the control unit may confirm whether the second image data is aligned with the first grouped data.

Meanwhile, when the updated number of alignment attempts is 10 or more, the alignment unit may determine that the second image data may not be aligned with the first grouped data and the data gap has occurred. In this case, the alignment unit may stop the attempt to align the second image data with the first grouped data any longer, and the grouped data management unit may generate the new grouped data. In other words, when the second image data is not aligned with the first grouped data the predetermined number of times or for the predetermined time, the grouped data management unit may generate the second grouped data different from the first grouped data to include the second image data (S235). The second image data is included in the second grouped data, so that the user may continuously perform the scan even without necessarily finding a position aligned with the first grouped data and performing the scan using the scanner.

As described above, the limitation condition of the alignment attempt has been described as the number of times, but is not limited thereto, and it is also possible to set the alignment attempt time as a critical condition. In addition, the order of the operation of updating the number of alignment attempts and the operation of confirming whether the updated number of alignment attempts is less than the critical number of times may be changed. For example, when the second image data is not aligned with the first grouped data in the operation of confirming whether the second image data is aligned with the first grouped data (S231), the control unit may determine whether the number of alignment attempts is less than the critical number of times, and update the number of alignment attempts when the number of alignment attempts is less than the critical number of times. After the number of alignment attempts is updated, the operation of confirming whether the second image data is aligned with the first grouped data (S231) may be performed again.

Typically, the user wants to generate the grouped data according to his/her intention. However, when the scan environment (illuminance, foreign substances, or the like) is changed or the scanner is moved quickly, there occurs a case in which the data gap instantaneously occurs. The generation of the new grouped data whenever the data gap instantaneously occurs is not only contrary to the user's intention but also causes an increase in the amount of operations for acquiring and aligning the image data and generating the grouped data. As the amount of operations increases, a scan speed of the scanner may decrease, thereby lowering scanning efficiency.

Accordingly, in still another embodiment of the present disclosure, when the second image data is not aligned with the first grouped data, the new grouped data is not immediately generated, and the user's intention may be confirmed through the predetermined number of alignment attempts or the predetermined alignment attempt time. In other words, even when the instantaneous alignment failure that the user does not want occurs, the grouped data management unit may prevent the new grouped data from being unnecessarily generated when the image data aligned with the first grouped data within the predetermined number of alignment attempts or the predetermined alignment attempt time is input.

When the second image data is not aligned with the first grouped data according to the user's intention, the new grouped data may be generated. For example, when the user scans a right molar part and then moves to a left molar part to perform the scan, the data gap may occur between the right molar part and the left molar part. In this case, the image data representing the right molar part and the image data representing the left molar part are not aligned, and this state exceeds the predetermined number of alignment attempts or the predetermined alignment attempt time. Accordingly, the appropriate number of grouped data may be generated according to the user's intention using the predetermined number of times or the predetermined time. The user may perform the scan in a desired way without caring whether the alignment is performed, and finally acquire a sophisticated three-dimensional model.

In addition, when the second grouped data is generated, the operation of combining the second grouped data and the first grouped data (S240) may be performed. The operation of combining the second grouped data and the first grouped data (S240) may be performed by the alignment unit and the grouped data management unit of the control unit. Each of the first image data included in the first grouped data and the second image data included in the second grouped data may form the three-dimensional volume data, and each of the three-dimensional volume data may configure at least a part of the overall three-dimensional model. Accordingly, all grouped data may be aligned to complete one three-dimensional model.

Meanwhile, since the first image data included in the first grouped data and the second image data included in the second grouped data do not overlap, the alignment may not be performed. In other words, the data gap may exist between the first grouped data and the second grouped data. In this case, the alignment may be performed through the third image data overlapping at least a partial area of the first image data and at least a partial area of the second image data, respectively. For example, the third grouped data may be generated between the first grouped data and the second grouped data, and the third grouped data may include the third image data. The third image data may be aligned with both the first grouped data and the second grouped data by the alignment unit. Accordingly, the first grouped data and the second grouped data may be aligned via the third grouped data. However, this is only illustrative, and a plurality of grouped data may also be generated between the first grouped data and the second grouped data to eliminate the data gap.

Hereinafter, a grouped data alignment device for performing the above-described aligning method by grouped data will be described.

Figure 9:
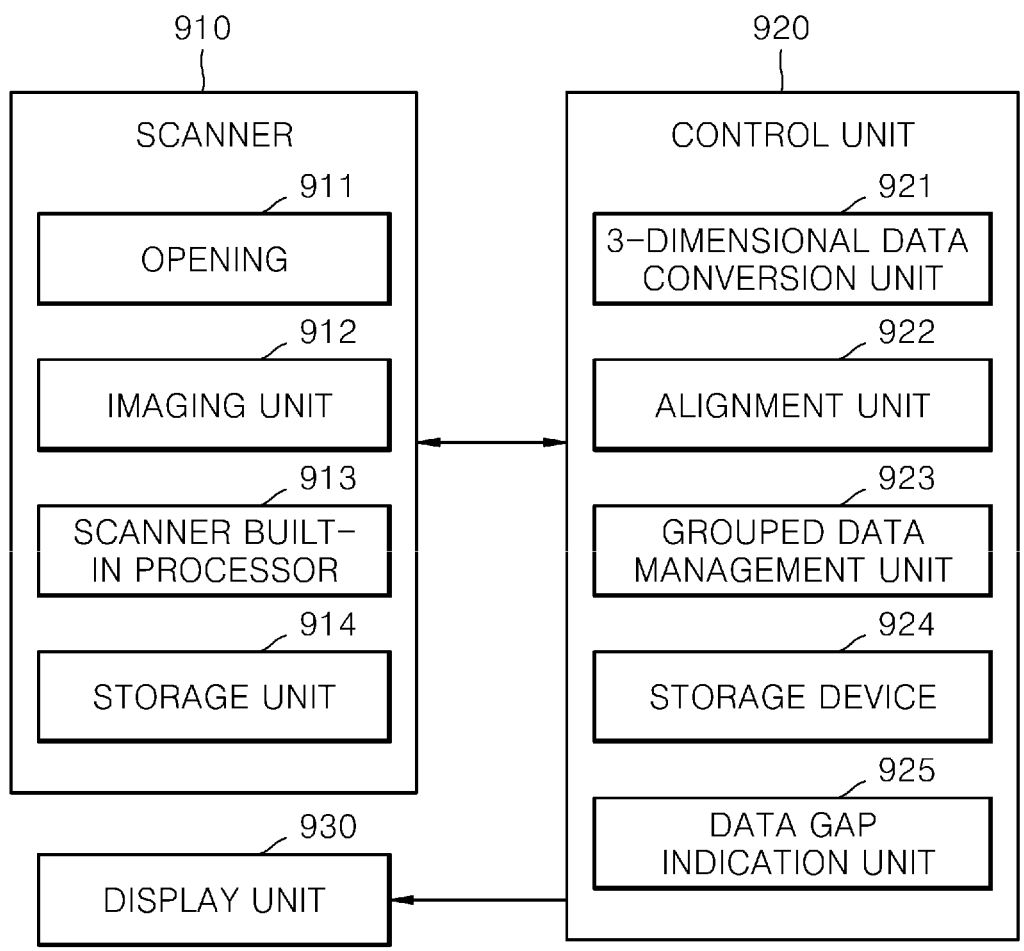
FIG. 9 is a configuration view of a grouped data alignment device for performing the aligning method by grouped data according to the present disclosure.

FIG. 9 is a configuration view of a grouped data alignment device for performing the aligning method by grouped data according to the present disclosure.

Referring to FIG. 9, a grouped data alignment device 900 for performing the aligning method by grouped data according to the present disclosure may include a scanner 910, a control unit 920, and a display unit 930.

The scanner 910 may acquire image data by scanning an object to be scanned. For example, the scanner 910 may be a handheld scanner that may be gripped by a user to scan the inside of the patient's oral cavity at a free scan angle and scan distance.

More specifically, when the user scans the inside of the patient's oral cavity through the scanner 910, light reflected from the teeth or gums inside the oral cavity is incident into the scanner 910 through an opening 911 formed at one end thereof. Light incident into the scanner 910 is received by at least one imaging unit 912 formed inside the scanner 910. At this time, the imaging unit may include at least one camera and an imaging sensor electrically connected to the camera, and image data may be generated by the imaging unit.

The scanner 910 may include a scanner built in processor 913. The scanner built-in processor 913 may generate initial grouped data (first grouped data) when starting a scan process through the scanner 910. However, in some cases, the initial grouped data may also be generated by the control unit 920 to be described later.

In addition, the scanner built-in processor 913 may control the image data generated by the imaging unit 912 to be stored in a storage unit 914. In addition, the scanner built-in processor 913 may control the scanner 910 to transmit the image data generated by the imaging unit 912 to the control unit 920.

In addition, the scanner 910 may include the storage unit 914. The storage unit 914 may store the image data generated by the imaging unit 912. The storage unit 914 may be formed to be built in the scanner 910, and a known storage element such as an SSD or a memory card may be used.

Hereinafter, a detailed configuration of the control unit 920 will be described.

The control unit 920 may generate and manage at least one grouped data including image data, convert tow-dimensional image data into three-dimensional volume data, and perform alignment between the three-dimensional volume data. In addition, in some cases, the control unit 920 may also control the remaining data gap to be displayed on the display unit 930 so that the user may easily confirm the data gap between the grouped data.

The control unit 920 may include a three-dimensional data conversion unit 921. The three-dimensional data conversion unit 921 may convert the image data acquired in the above-described image generating operation into three-dimensional volume data. The three-dimensional data conversion unit 921 may convert the image data acquired from the imaging unit 912 into three-dimensional data including voxel data using pixel brightness information and the like of the two-dimensional image data acquired from the imaging unit 912.

The control unit 920 may include an alignment unit 922. The alignment unit 922 may connect and align the image data converted by the three-dimensional data conversion unit 921. In addition, the alignment unit 922 may determine whether newly acquired second image data is aligned with the first grouped data, determine whether the second image data is in a disconnect state of being not aligned with the first grouped data the predetermined number of times or for a predetermined time, and control the grouped data management unit 923 to be described later to perform a predetermined operation. In addition, when the second image data is not aligned with the first grouped data the predetermined number of times or for the predetermined time, the alignment unit 922 may control the grouped data management unit 923 to recognize a point scanned just after the determination of the disconnect state as a start point of the corresponding scan path, and recognize a point scanned just before the determination of the disconnect state as an end point of the corresponding scan path. In addition, the alignment unit 922 may update the number of alignment attempts, and control the grouped data management unit 923 to generate new grouped data according to the relationship between the number of alignment attempts and the critical number of times.

In addition, the alignment unit 922 may combine the first grouped data and the second grouped data. For example, the alignment unit 922 may align at least a partial area of the first image data included in the first grouped data and at least a partial area of the second image data included in the second grouped data. As another example, the alignment unit 922 may combine the first grouped data and the second grouped data through third image data overlapping each of at least a partial area of the first image data included in the first grouped data and at least a partial area of the second image data included in the second grouped data.

In addition, the alignment unit 922 may detect the data gap for a part in which continuously acquired image data is not aligned, and control the data gap indication unit 925 to be described later so that the data gap indication unit 925 may visually indicate the data gap.

The control unit 920 may include the grouped data management unit 923. The grouped data management unit 923 may include specific image data in the grouped data according to the operation of the alignment unit 922. For example, when the second image data is aligned with the first image data included in the first grouped data by the alignment unit 922, the grouped data management unit 923 may categorize the second image data to be included in the first grouped data to store the categorized image data in the storage device 924. In addition, when the grouped data is aligned by the reconnection determining operation of checking whether the initial grouped data and the new grouped data overlap by the alignment unit 922, the grouped data management unit 923 may combine the grouped data. In addition, when the second image data is not aligned with the first grouped data the predetermined number of times or for the predetermined time by the alignment unit 922, the grouped data management unit 923 may generate second grouped data, which is new grouped data, and categorize the second image data to be included in the second grouped data and store the categorized second image data in the storage device 924.

The control unit 920 may include the storage device 924. The storage device 924 may store image data, three-dimensional volume data, grouped data, and the like, and at least one of known devices such as a hard disk drive, an SSD drive, and a flash drive may be used as the storage device 924.

The control unit 920 may include the data gap indication unit 925. The data gap indication unit 925 may indicate the point at which the data gap has occurred between the grouped data detected by the alignment unit 922 in a predetermined shape (e.g., an arrow shape). The point at which the data gap has occurred may be visually displayed on the display unit 930 to be clearly confirmed by the user by the data gap indication unit 925.

The display unit 930 may visually display at least a part of processes in which the above-described aligning method by grouped data is performed. For example, the display unit 930 may display the point a which the image data is not connected to each other, that is, the point at which the data gap has occurred, between the grouped data. In addition, the display unit 930 may display the aligning process by grouped data including the process of aligning the image data. The known visual display device may be used as the display unit 930, and a detailed description of the type of the display unit 930 will be omitted.

The above description is merely illustrative of the technical spirit of the present disclosure, and various modifications and changes will be possible without departing from the essential characteristics of the present disclosure by those skilled in the art to which the present disclosure pertains.

Accordingly, the embodiments disclosed in the present disclosure are not intended to limit the technical spirit of the present disclosure, but are intended to describe the same, and the scope of the technical spirit of the present disclosure is not limited by these embodiments. The scope of the present disclosure should be construed by the following claims, and all technical spirits within the scope equivalent thereto should be construed as being included in the scope of the present disclosure.

INDUSTRIAL APPLICABILITY

The aligning method by grouped data according to the present disclosure provides the method capable of acquiring the entire three-dimensional model through the alignment between the grouped data by categorizing the aligned image data into the grouped data even when the image data acquired along the scan process are not continuously aligned.

The invention claimed is:

1. An aligning method by grouped data, the method comprising:
   generating a first grouped data including at least one first image data through a scanner;
   determining whether a second image data is aligned with the first grouped data by a control unit;
   including the second image data in the first grouped data when the second image data is aligned with the first grouped data by the control unit;
   attempting alignment a predetermined number of times or for a predetermined time when the second image data is not aligned with the first grouped data by the control unit;
   generating a second grouped data to include the second image data when the second image data is not aligned with the first grouped data the predetermined number of times or for the predetermined time by the control unit; and
   combining the first grouped data and the second grouped data by the control unit,
   wherein the first image data and the second image data are parts of one of one mandibular data, one maxillary data, and occlusal data obtained by combining the mandibular and maxillary data.

2. The method of claim 1,
   wherein the first image data and the second image data are converted into three-dimensional volume data.

3. The method of claim 1,
   wherein the attempting of the alignment includes confirming whether the second image data is aligned with the first grouped data for the predetermined time; and
   updating the number of alignment attempts when the second image data is not aligned with the first grouped data in the confirming of whether the second image data is aligned with the first grouped data.

4. The method of claim 3, further comprising: confirming whether the updated number of alignment attempts is less than the critical number of times by the control unit, wherein the process returns to confirming whether the second image data is aligned with the first grouped data when the number of alignment attempts is less than the critical number of times.

5. The method of claim 4, wherein the control unit generates the second grouped data to include the second image data when the number of alignment attempts is greater than or equal to the critical number of times.

6. The method of claim 1, wherein in the combining of the first grouped data and the second grouped data, at least a partial area of the first image data included in the first grouped data and at least a partial area of the second image data included in the second grouped data are aligned.

7. The method of claim 6, wherein the first image data and the second image data are aligned through a third image data that overlaps each of the at least the partial area of the first image data and the at least the partial area of the second image data.

8. An aligning method by grouped data, the method comprising:
   an image generating operation of acquiring an image along a scan path through a scanner;
   an aligning operation of aligning the image data continuously acquired along the scan path to be connected to each other by a control unit;
   a grouped data storing operation of making the image data a grouped data and categorizing and storing the grouped data based on a point at which the image data are disconnected to each other in the aligning operation by the control unit; and
   a reconnection determining operation of aligning data of the two or more grouped data to be connected to each other by the control unit,
   wherein the image data is a part of one of one mandibular data, one maxillary data, and occlusal data obtained by combining the mandibular and maxillary data.

9. The method of claim 8, wherein the point at which the image data are disconnected is determined according to an overlapping range of the continuous image data in the grouped data storing operation.

10. The method of claim 8, wherein the scan path includes a plurality of paths, the plurality of paths have different start points and end points, and the plurality of paths have a scan area overlapping in at least some sections.

11. The method of claim 10, wherein the number of grouped data stored in the grouped data storing operation has the number according to the plurality of scan paths.

12. The method of claim 10, wherein the point at which the image data is disconnected to each other in the aligning operation is the end point of each scan path.

13. The method of claim 8, further comprising: displaying the point at which the image data is disconnected to each other between the grouped data on a display unit by the control unit.

* * * * *